(12) United States Patent
Daniel et al.

(10) Patent No.: US 7,399,299 B2
(45) Date of Patent: Jul. 15, 2008

(54) THERMAL ABLATION OF BIOLOGICAL TISSUE

(75) Inventors: Steven A. Daniel, Fremont, CA (US); David L. Morris, Lugamo (AU)

(73) Assignee: S.D.M.H. Pty. Ltd., Sydney (AU)

( * ) Notice: Subject to any disclaimer, the term of this patent is extended or adjusted under 35 U.S.C. 154(b) by 0 days.

(21) Appl. No.: 10/889,756

(22) Filed: Jul. 12, 2004

(65) Prior Publication Data
US 2005/0049586 A1 Mar. 3, 2005

Related U.S. Application Data

(60) Provisional application No. 60/486,874, filed on Jul. 11, 2003.

(51) Int. Cl.
*A61B 18/18* (2006.01)

(52) U.S. Cl. ............................................. 606/41

(58) Field of Classification Search ............ 606/27–52; 607/101, 102, 115, 116; 604/21, 22
See application file for complete search history.

(56) References Cited

U.S. PATENT DOCUMENTS

| | | |
|---|---|---|
| 4,346,715 A | 8/1982 | Gammell |
| 5,536,267 A | 7/1996 | Edwards |
| 5,545,193 A | 8/1996 | Fleischman |
| 5,672,174 A | 9/1997 | Gough |
| 5,683,384 A | 11/1997 | Gough |
| 5,728,143 A | 3/1998 | Gough |
| 5,800,484 A | 9/1998 | Gough |
| 5,863,290 A * | 1/1999 | Gough et al. ............. 606/41 |
| 5,925,042 A | 7/1999 | Gough |
| 5,938,694 A | 8/1999 | Jaraczewski |
| 5,980,517 A * | 11/1999 | Gough |
| 6,001,093 A | 12/1999 | Swanson |
| 6,059,780 A | 5/2000 | Gough |
| 6,071,280 A | 6/2000 | Edwards |
| 6,235,023 B1 | 5/2001 | Lee |
| 6,330,478 B1 | 12/2001 | Lee |
| 6,454,765 B1 | 9/2002 | Leveen |
| 6,468,273 B1 | 10/2002 | Leveen |
| 6,471,698 B1 | 10/2002 | Edwards |
| 6,569,159 B1 | 5/2003 | Edwards |
| 6,575,967 B1 | 6/2003 | Leveen |
| 6,623,481 B1 * | 9/2003 | Garbagnati et al. ........... 606/41 |
| 6,638,277 B2 | 10/2003 | Schaefer |
| 6,958,062 B1 | 10/2005 | Gough |
| 7,025,767 B2 | 4/2006 | Schaefer |

FOREIGN PATENT DOCUMENTS

GB   WO 95/02370   * 1/1995

* cited by examiner

*Primary Examiner*—Roy D. Gibson
*Assistant Examiner*—Peter J Vrettakos
(74) *Attorney, Agent, or Firm*—Courtney Staniford & Gregory LLP (57) ABSTRACT

An ablation device is described comprising an introducer and an electrode array. The electrode array couples to a distal end of the introducer. The electrode array includes a center member having a distal end configured to penetrate tissue and a plurality of electrodes. Proximal and distal ends of each electrode are relatively fixed. The electrodes are dynamically configurable from a retracted state to a deployed state in which the electrodes form a relatively spherical shape in a tissue volume.

19 Claims, 12 Drawing Sheets

THERMAL ABLATION OF BIOLOGICAL TISSUE

RELATED APPLICATION

This application claims priority from U.S. patent application Ser. No. 60/486,874, filed Jul. 11, 2003.

TECHNICAL FIELD

This invention relates generally to devices and methods for tissue ablation, and more particularly to the creation of spherical ablations in biological tissue.

BACKGROUND

Standard surgical procedures such as tissue resection for use in treatment of benign and malignant tumors of the liver and other organs have several key shortcomings affecting efficacy, morbidity and mortality. A fundamental issue in these shortcomings is the inability of the resection to be performed in a variety of cases. To help overcome this limitation a series of mono-polar radio frequency (RF) devices were designed for use in tissue ablation and resection. These mono-polar devices however have limited usefulness in typical clinical settings because they are overly complex and difficult to use and result in time consuming procedures that can lead to auxiliary injury to patients through grounding pad burs. Further, these mono-polar tissue ablation devices are limited in the scope and size of the ablation that can be created, and exhibit poor consistency of ablative results along with an overall low efficiency. Consequently, there is a need for a tissue ablation system that overcomes the shortcomings of these mono-polar tissue ablation devices.

In the drawings, the same reference numbers identify identical or substantially similar elements or acts. To easily identify the discussion of any particular element or act, the most significant digit or digits in a reference number refer to the Figure number in which that element is first introduced (e.g., element 108 is first introduced and discussed with respect to FIG. 1).

DETAILED DESCRIPTION

A tissue ablation system including numerous components and methods is described herein for generating tissue ablation volumes in various biological tissues. The biological tissue includes tissue of a variety of organs of the human body including the liver, spleen, kidney, lung, breast and other organs, but is not so limited. In the following description, numerous specific details are introduced to provide a thorough understanding of, and enabling description for, embodiments of the tissue ablation system. One skilled in the relevant art, however, will recognize that the tissue ablation system can be practiced without one or more of the specific details, or with other components, systems, etc. In other instances, well-known structures or operations are not shown, or are not described in detail, to avoid obscuring aspects of the tissue ablation system.

Figure 1:
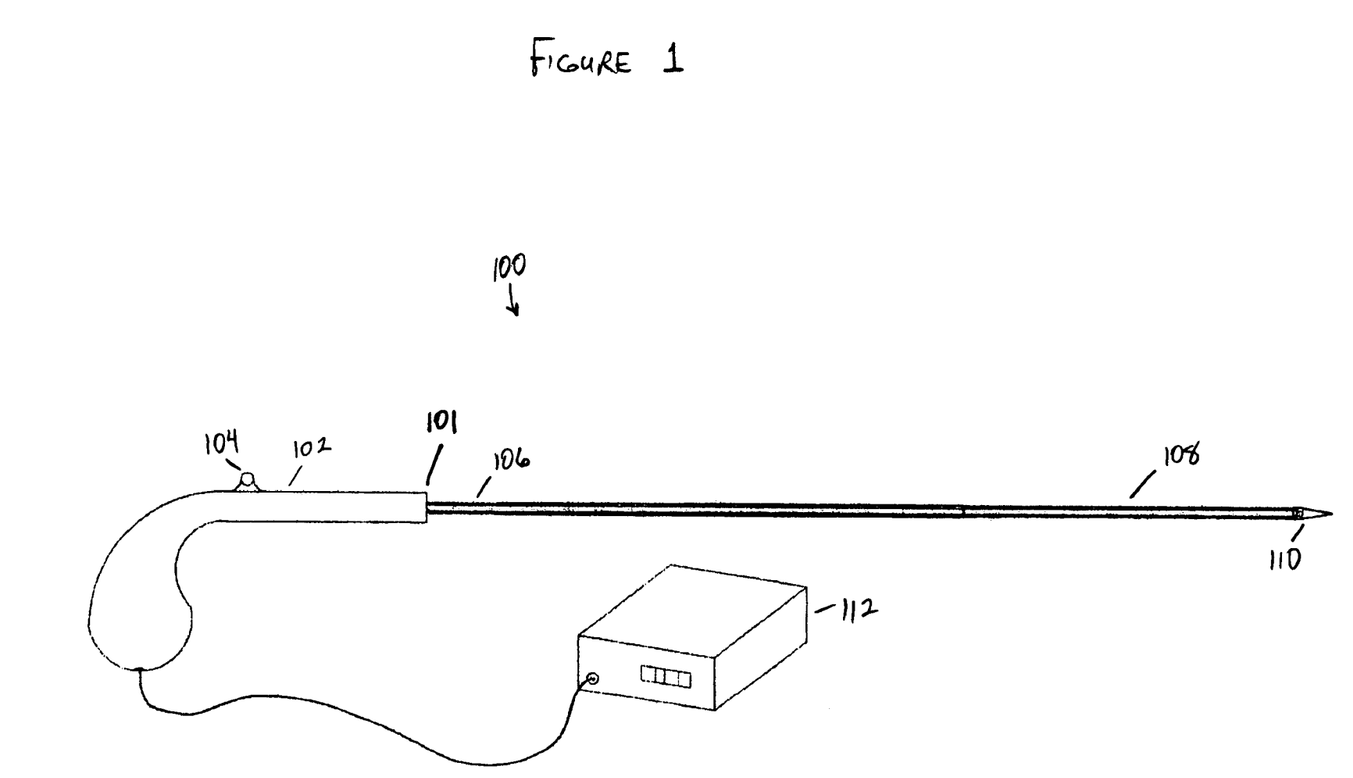
FIG. 1 is a tissue ablation device including a hand piece, a deployment slider, a delivery member/tube, and a plurality of energy conduits in a retracted state coupled among an energy source and a distal tip, under an embodiment.
Figure 2:
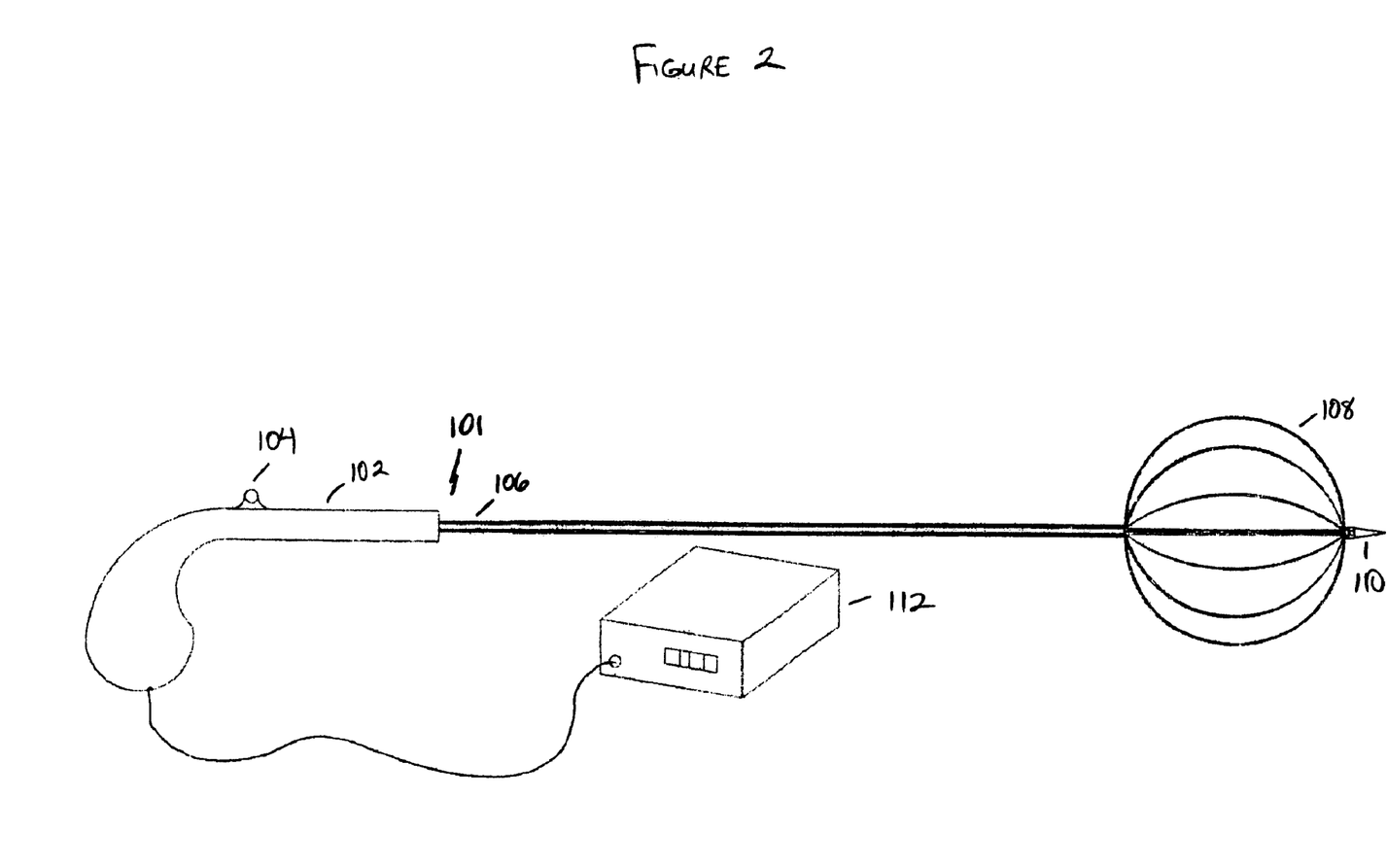
FIG. 2 is a tissue ablation device including a hand piece, a deployment slider, a delivery member/tube, and a plurality of energy conduits in a deployed state coupled among an energy source and a distal tip, under the embodiment of FIG. 1.

FIG. 1 is a tissue ablation system 100, under an embodiment. The tissue ablation system 100 includes a tissue ablation device 101 coupled to at least one energy source 112. The tissue ablation device 101 includes a hand piece 102, a deployment slider 104, a delivery member/tube 106, a plurality of energy conduits 108, and a distal tip 110, under an embodiment. The energy conduits 108, also referred to herein as electrodes 108, are in a retracted state, but are not so limited. FIG. 2 is a tissue ablation device with the energy conduits 108 in a deployed state, under an embodiment. The tissue ablation device 101 can also include other components as known in the art and as appropriate to procedures including the tissue ablation device 101.

The components of the tissue ablation system 100 are described in turn with reference to FIG. 1 and FIG. 2. The hand piece 102 of the tissue ablation device 101 includes a handle by which the user grips the tissue ablation device 101. The hand piece 102 provides a coupling between the energy source 112 and one or more of the energy conduits 108 which may or may not be coupled to at least one of the hand piece 102 and the energy source 112. The deployment slider 104 or advancement mechanism 104, which in an embodiment is integral to the hand piece 102, deploys or retracts the energy conduits 108 upon actuation.

The tissue ablation device 101 also includes a delivery member/tube 106 that supports placement of the energy conduits 108 in the target tissue, but is not so limited.

The delivery member/tube 106 is formed using material that is at least one of electrically conductive, conditioned, and coated to allow for electrical conductivity via the electrodes. As an example, the delivery member/tube 106 is formed using at least one of stainless steel, nickel titanium, alloys, and plastics including Ultem, Polycarbonate, and Liquid crystal polymer, but is not so limited. The delivery member/tube 106 has a diameter approximately in a range of 0.05 to 0.5 inches, and has a length approximately in a range of 0.1 to twenty (20) inches as appropriate for extension into a body region appropriate to the treatment procedure. As one example, the delivery member/tube 106 of an embodiment has a diameter of between approximately 0.08 and 0.3 inches and a length between approximately two (2) and twelve (12) inches.

The energy conduits 108 while configured appropriately for insertion into particular tissue types, are formed from one or more materials and have a shape, size, and pattern that supports coupling to the target tissue and allows the energy conduits 108 to deliver sufficient energy to ablate the target tissue. The energy conduits 108 include materials selected from among conductive or plated metals and/or plastics, super alloys including shape memory alloys, and stainless steel, to name a few. The energy conduits 108 comprise nickel titanium alloy, for example, but can be formed from any number/combination of materials including stainless steel, nickel titanium, and various alloys.

The energy conduits 108 of an embodiment, which collectively may be referred to as an electrode array 108, can have many different sizes (including lengths and diameters) depending upon the energy delivery parameters (current, impedance, etc.) of the corresponding system. The use of energy conduits 108 having different diameters allows for balancing of energy/energy density in the target tissue. Therefore, the use of energy conduits 108 having different diameters provides a means of control over energy balancing in the target tissue in addition to the spacing between the energy conduits 108. An outside diameter of one or more of the energy conduits 108 of an embodiment is approximately in the range of 0.005 to 0.093 inches, but is not so limited. Further, the energy conduits 108 of an embodiment have lengths sufficient to generate or create an ablation diameter approximately in the range of one (1) to fifteen (15) centimeters (cm), but are not so limited. As one example, the energy conduits 108 of an embodiment have an outside diameter between approximately 0.01 and 0.025 inches and lengths sufficient to generate or create an ablation diameter approximately in the range of three (3) to nine (9) centimeters (cm).

The energy conduits 108 of various alternative embodiments can include materials that support bending and/or shaping of the energy conduits 108. Further, the energy conduits 108 of alternative embodiments can include non-conducting materials, coatings, and/or coverings in various segments and/or proportions along the shaft of the energy conduits 108 as appropriate to the energy delivery requirements of the corresponding procedure and/or the type of target tissue The energy source 112 of an embodiment (also referred to as a generator 112 or electrical generator 112) delivers pre-specified amounts of energy at selectable frequencies in order to ablate tissue, but is not so limited. The energy source 112 includes at least one of a variety of energy sources including electrical generators operating within the radio frequency (RF) range. More specifically, the energy source 112 includes an RF generator operating in a frequency range of approximately 375 to 650 kHz and at a current of approximately 0.1 to 5 Amps and an impedance of approximately 5 to 100 ohms, but is not so limited. As an example, the energy source 112 of an embodiment operates at a frequency approximately in the range of 400 kHz to 550 kHz and at a current of approximately 0.5 to four (4) Amps, but is not so limited. Variations in the choice of electrical output parameters from the energy source 112 to monitor or control the tissue ablation process may vary widely depending on tissue type, operator experience, technique, and/or preference.

The tissue ablation system 100 can include any number of additional components like, for example, a controller (not shown) to semi-automatically or automatically control delivery of energy from the energy source 112. The controller can, for example, increase the power output to the energy conduits 108, control temperature when the energy conduits 108 include temperature sensors or when receiving temperature information from remote sensors, and/or monitor or control impedance, power, current, voltage, and/or other output parameters. The functions of the controller can be integrated with those of the energy source 112, can be integrated with other components of the tissue ablation system 100, or can be in the form of stand-alone units coupled among components of the tissue ablation system 100, but are not so limited.

Moreover, the tissue ablation system 100 can include an operator display (not shown) that provides a display of heating parameters such as temperature for one or more of the energy conduits 108, impedance, power, current, timing information, and/or voltage of the energy source 112 output. The functions of the display can be integrated with those of the energy source 112, can be integrated with other components of the tissue ablation system 100, or can be in the form of stand-alone units coupled among components of the tissue ablation system 100, but are not so limited.

In operation a user advances the deployment slider 104 and in response the energy conduits 108 are forced, or in the case of a pre-shaped energy conduits released, from the retracted state to the deployed state. The shape of the deployed energy conduits can, as shown in FIG. 2, form a series of approximately semi-spherical segments that, when taken together, form the outline of a sphere. The tissue ablation device generates a spherical volume of ablated tissue upon application of energy to the deployed electrodes.

Figure 3:
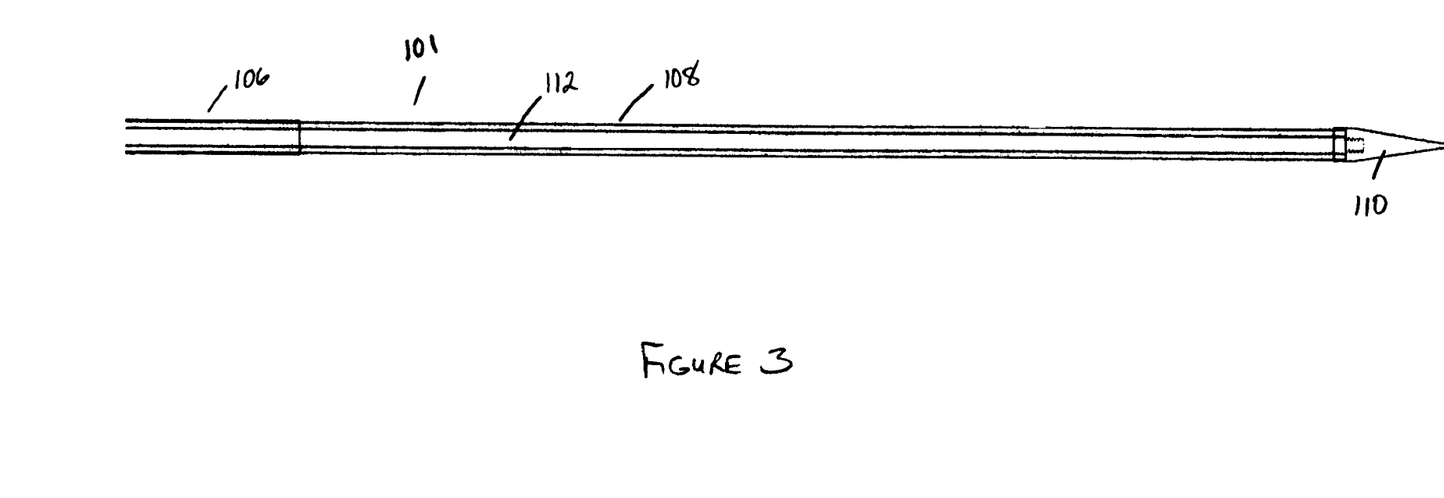
FIG. 3 is a distal portion of a tissue ablation device including a delivery member/tube and a plurality of energy conduits in a retracted state, under the embodiment of FIG. 1.

FIG. 3 is the distal portion of a tissue ablation device 101 including a delivery member/tube 106, a deployment member or rod 112, a plurality of energy conduits 108 in a retracted state (two energy conduits are shown for simplicity, but the embodiment is not so limited), and a distal tip 110, under the embodiment of FIG. 1. The energy conduits 108 are coupled, either individually or collectively, to an energy source or generator (not shown). When the energy conduits 108 are in the retracted state, the distal portion of the tissue ablation device presents a very streamline profile well suited to piercing tissue and advancement/placement in/near an area which might contain a malignant or non-malignant tumor. By piercing the tumor the distal tip can be placed just beyond the tumor.

Figure 4:
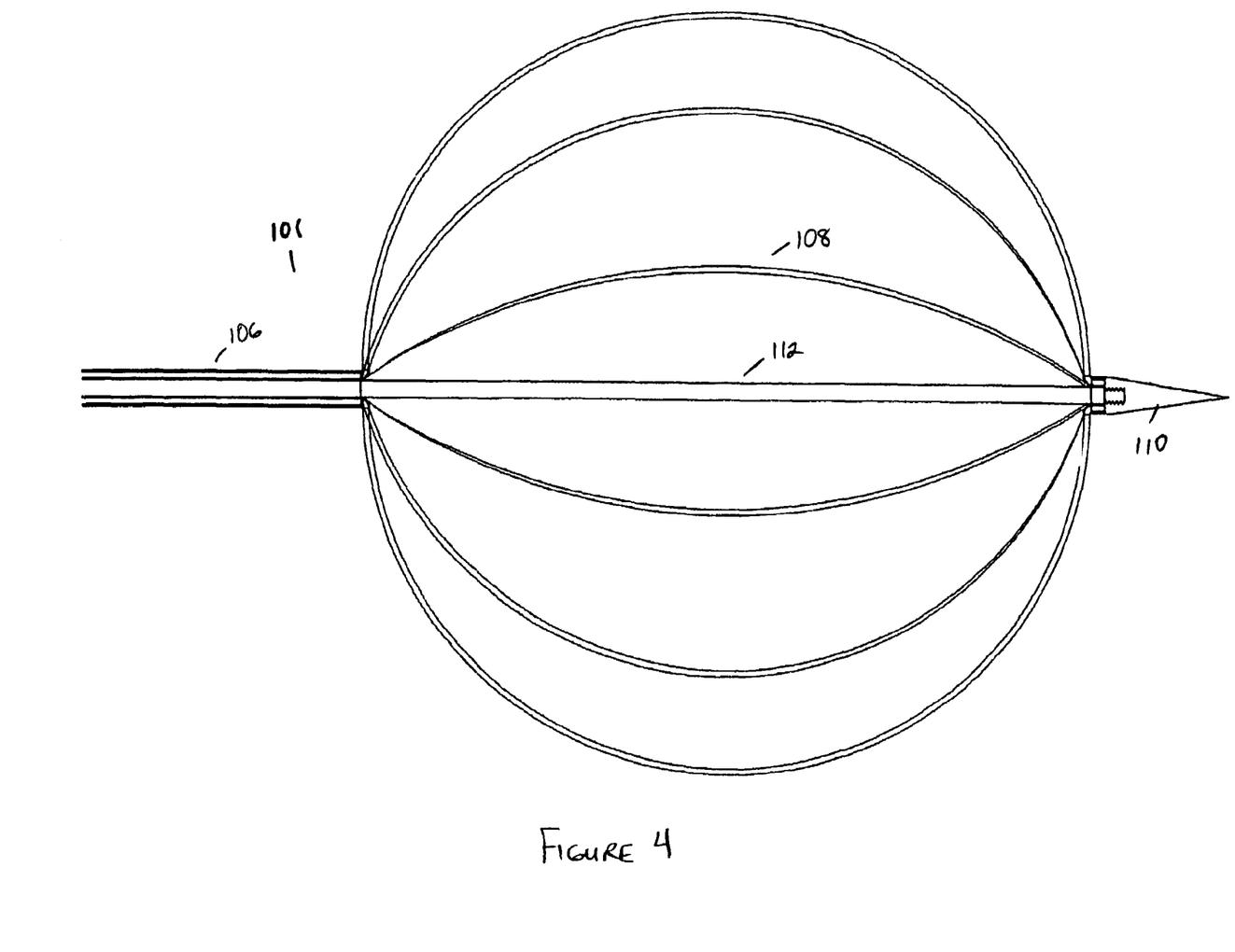
FIG. 4 is a distal portion of a tissue ablation device including a delivery member/tube and a plurality of energy conduits in a deployed state, under the embodiment of FIG. 1.

FIG. 4 is the distal portion of a tissue ablation device 101 including a delivery member/tube 106, a deployment member or rod 112, a plurality of energy conduits 108 in a deployed state, and a distal tip 110, under the embodiment of FIG. 1. The energy conduits 108 are coupled, either individually or collectively, to an energy source or generator (not shown). Following placement of the distal portion of the tissue ablation 10 device in the target tissue as appropriate to the corresponding medical procedure, the user advances the deployment slider (not shown) to deploy the energy conduits 108, thus fully encompassing the volume of tissue desired to be ablated.

Regarding deploying of the energy conduits 108, some or all of the energy conduits 108 can be deployed in response to advancement of the deployment slider. For example, all energy conduits 108 of an embodiment are deployed simultaneously in response to advancement of the deployment slider. As another example, one set of energy conduits 108 can be deployed to form a sphere having a first diameter while another set of energy conduits 108 can be deployed to form a sphere having a second diameter. Other alternative embodiments can use additional deployment schemes known in the art. 20 The energy conduits 108 of an embodiment deliver radio frequency (RF) current to the target tissue and, as such, can be of alternating electrical polarity. The alternating polarity series of energy conduits includes various series combinations of alternating polarities. For example, in an embodiment using ten (10) energy conduits, the alternating polarity is: positive polarity (+), negative polarity (−), +, −, +, −, +, −, +, −. An alternative polarity series is: +, +, −, −, +, +, −, −, +, +. Another alternative polarity series is: −, −, +, +, −, −, +, +, −, −. Yet another alternative polarity series is: +, +, +, +, +, −, −, −, −, −. These examples are exemplary only, and the tissue ablation system 100 described herein is not limited to ten (10) electrodes or to these alternating polarity configurations.

The energy conduits of an alternative embodiment conduct electricity of a single electrical polarity, with the deployment rod 112 conducts electricity having an opposite polarity to that of the energy conduits. In still another alternative embodiment, the deployable energy conduits are switched between the same electrical polarity with the deployment rod being the other and alternating polarity between the deployable energy conduits. In yet another alternative embodiment, the deployment rod and deployable energy conduits are of a single electrical polarity and one or more secondary grounding pads are used therewith to provide an opposite polarity member.

Various alternative embodiments can simultaneously use any number of energy conduits in a procedure in order to form volumes of ablated tissue having shapes and sizes appropriate to the treatment procedure. Numerous alternatives would be recognized by those skilled in the art in view of the tissue ablation device described herein.

Figure 5:
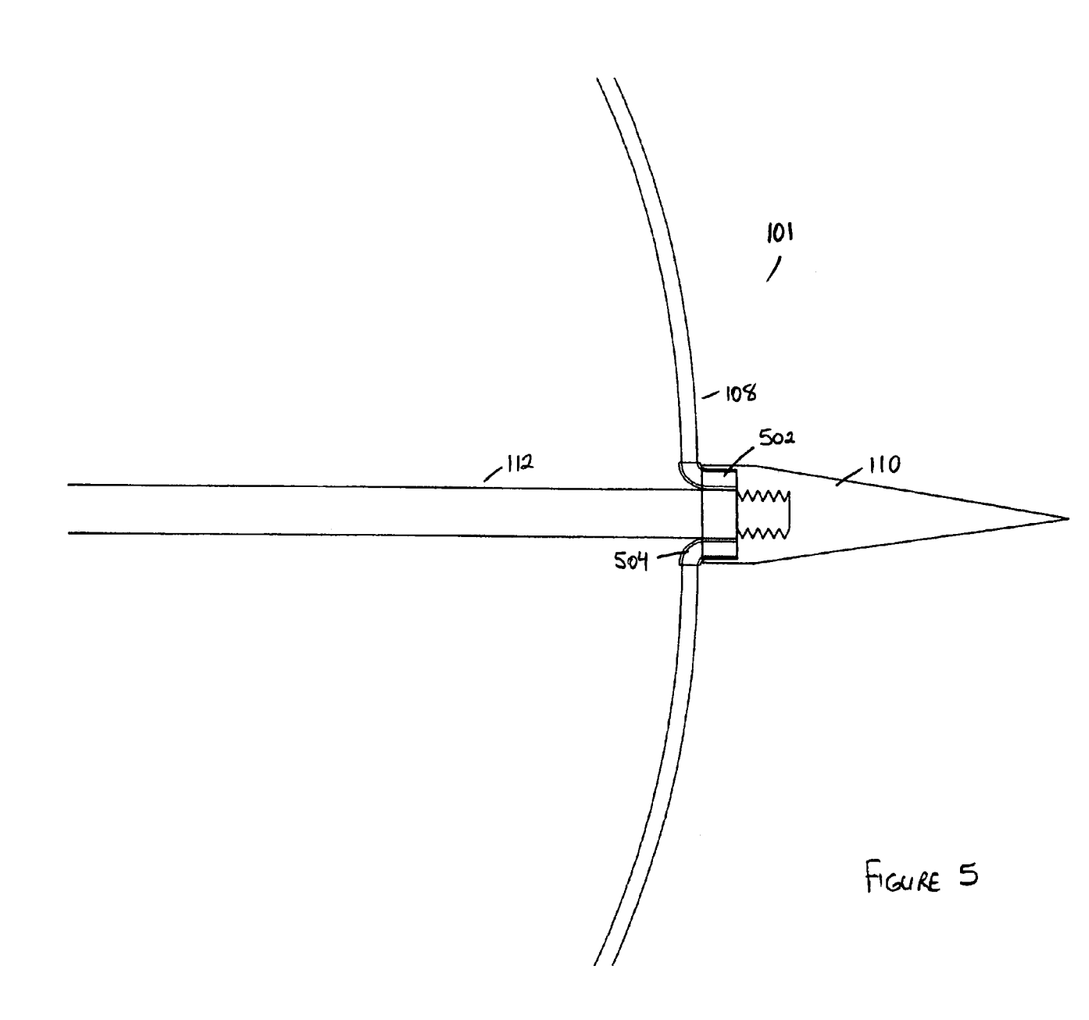
FIG. 5 shows an enlarged view of the distal portion of a tissue ablation device including a center deployment rod and a plurality of energy conduits in a deployed state, under the embodiment of FIG. 1.

FIG. 5 shows a distal region or portion of a tissue ablation device 101 including a center deployment rod 112, a plurality of energy conduits 108 in a deployed state (two energy conduits are shown for simplicity, but the embodiment is not so limited), conduit insulators 504, and a distal tip 110, under the embodiment of FIG. 1. In support of delivering electrical energy of alternating polarity via the energy conduits 108, the conduit insulators 504 mechanically couple the distal ends of the energy conduits 108 while maintaining electrical insulation between each of the energy conduits 108. In this tissue ablation device the deployable energy conduits 108 are coupled to the conduit insulators 504. The combination of the energy conduits 108 and the conduit insulators 504 is coupled to a non-electrically conductive retaining disk 502 that is coupled to an electrically conductive deployment member 112. Also connected to the deployment member 112 is the electrically conductive distal tip 110 that, in this embodiment, is suitable for piercing tissue. Advancing the deployment slider causes the deployable energy conduits or electrodes 108 to experience a compressive load. As this force increases beyond the column strength of the deployable energy conduits 108, the energy conduits 108 buckle and deploy outward in a controlled fashion.

Alternatively, the energy conduits 108 can be pre-formed to a desirable shape when fabricated of a suitable material such as a nickel titanium alloy. Using the pre-formed electrodes, advancement of the deployment slider permits the deployable electrodes to return to their preformed shape. The application of a small amount of energy such as RF current can help to facilitate the deployment of the electrodes through the tissue.

Figure 6:
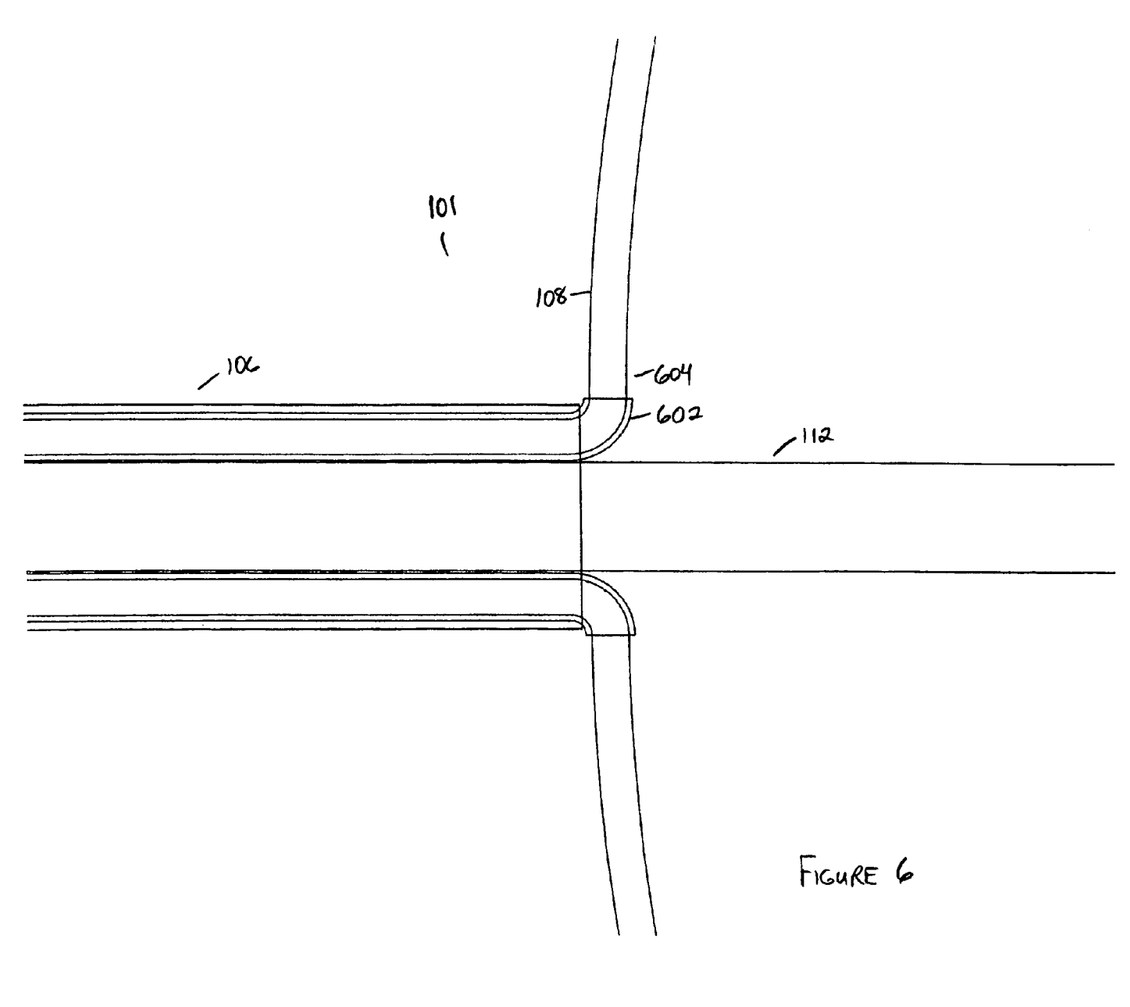
FIG. 6 shows an enlarged view of the mid-section of a tissue ablation device including a center deployment rod and a plurality of energy conduits in a deployed state, under the embodiment of FIG. 1.

FIG. 6 shows a mid-section of a tissue ablation device 101 including a delivery member/tube 106, a deployment member 112, and a plurality of energy conduits 108 in a deployed state (two energy conduits are shown for simplicity, but the embodiment is not so limited), under the embodiment of FIG. 1. The proximal end 604 of the energy conduits 108 couples to an electrical insulator 602 or insulating material 602, but is not so limited.

Figure 7:
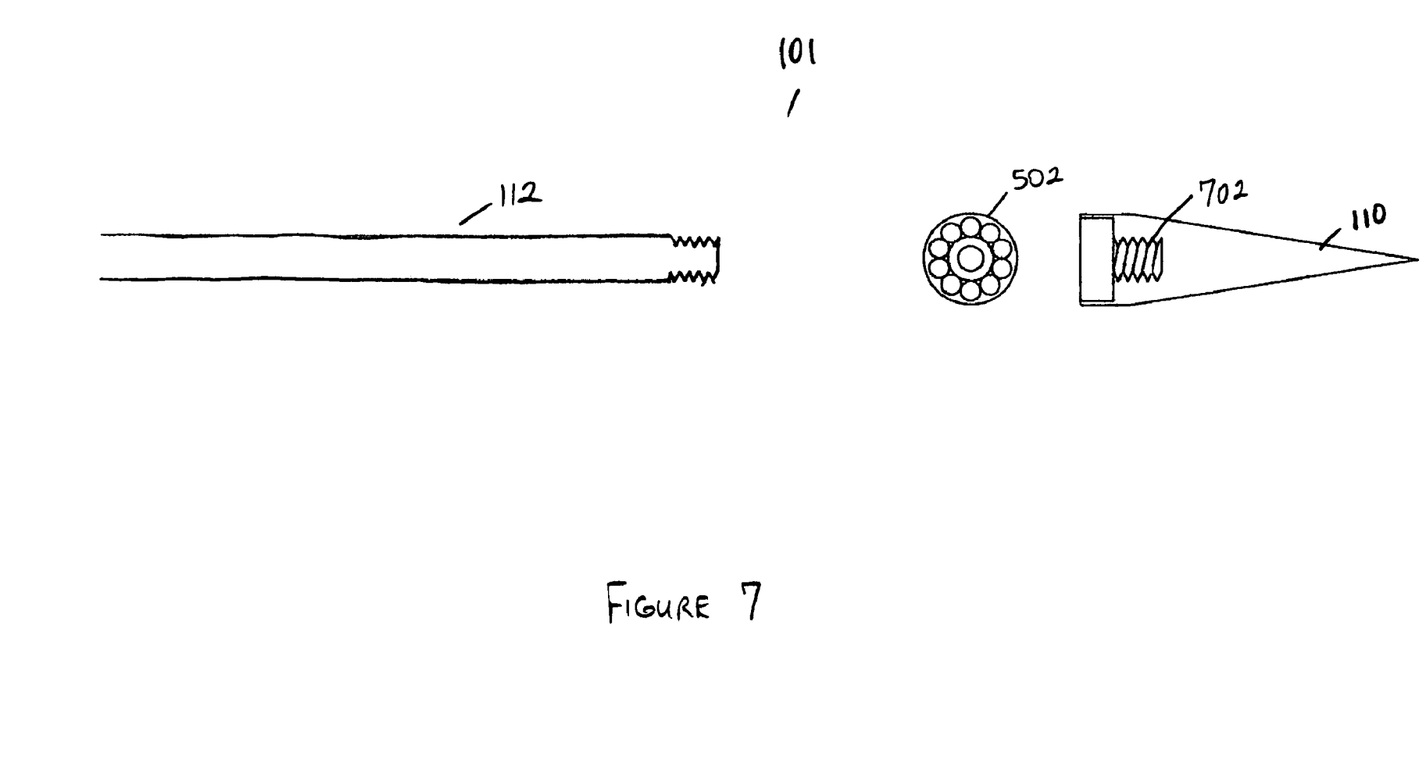
FIG. 7 shows an exploded view of the distal end of a tissue ablation device including a center deployment rod along with a rotated side view of the delivery member/tube including a plurality of energy conduits and deployment rod, and a distal tip, under the embodiment of FIG. 1.

FIG. 7 shows an exploded view of a distal region of a tissue ablation device 101 including a deployment member 112, a distal tip 110, and a rotated side view of an energy conduit retaining disk 502, under the embodiment of FIG. 1. Although a variety of methods exists to couple the components of the tissue ablation device 101 at the distal end, one such method is a simple screw thread 702 configured to accept a distal end of the deployment member 112. Alternatively, a press or interference fit between mating parts or the use of various adhesives can also be used. The retaining disk 502, as described above with reference to FIG. 5, is configured couple to the deployment member 112 and the distal tip 110.

Figure 8:
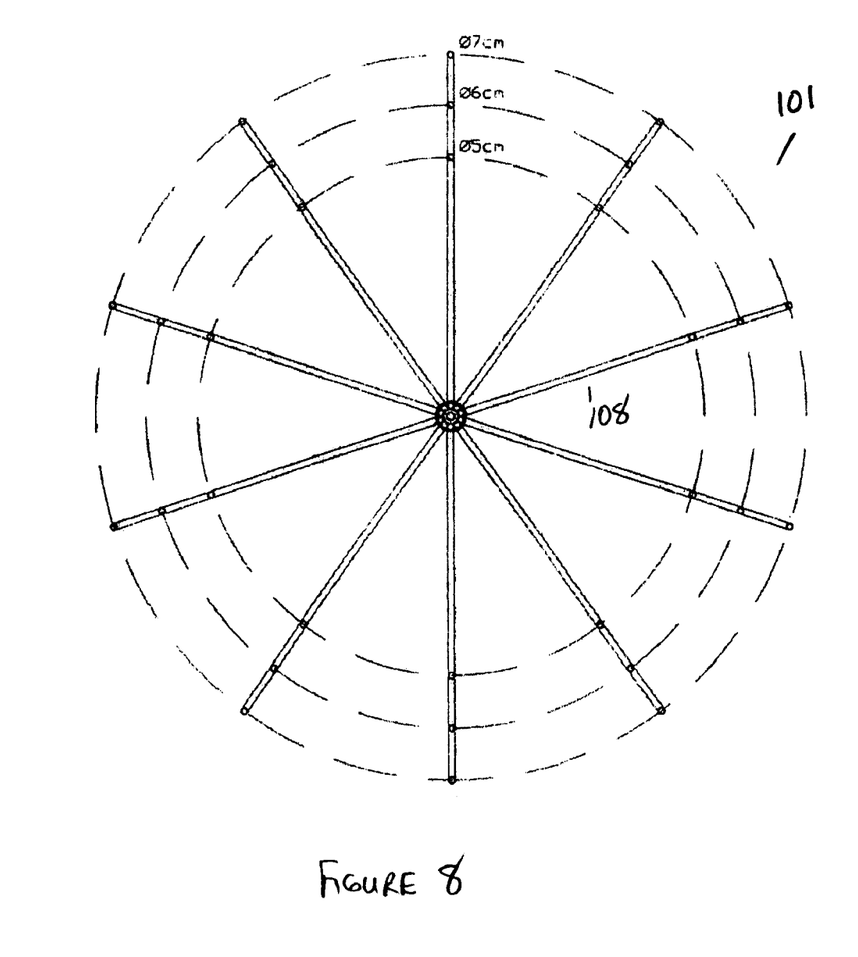
FIG. 8 is an end view of a plurality of deployed energy conduits having diameters of 5, 6, and 7 centimeters (cm), under the embodiment of FIG. 1.

FIG. 8 is an end view of a tissue ablation device 101 with deployed energy conduits 108 forming spheres having diameters of approximately 5, 6, and 7 centimeters (cm), under the embodiment of FIG. 1. The tissue ablation device 101 of an embodiment provides approximately uniform spacing among the energy conduits 108, but alternative embodiments may support any number/combination of energy conduit 108 configurations. The tissue ablation device 101 of an embodiment supports a variety of spherical deployment sizes by providing control over the extent to which the deployable energy conduits are deployed via the deployment slider, but is not so limited.

Figure 9:
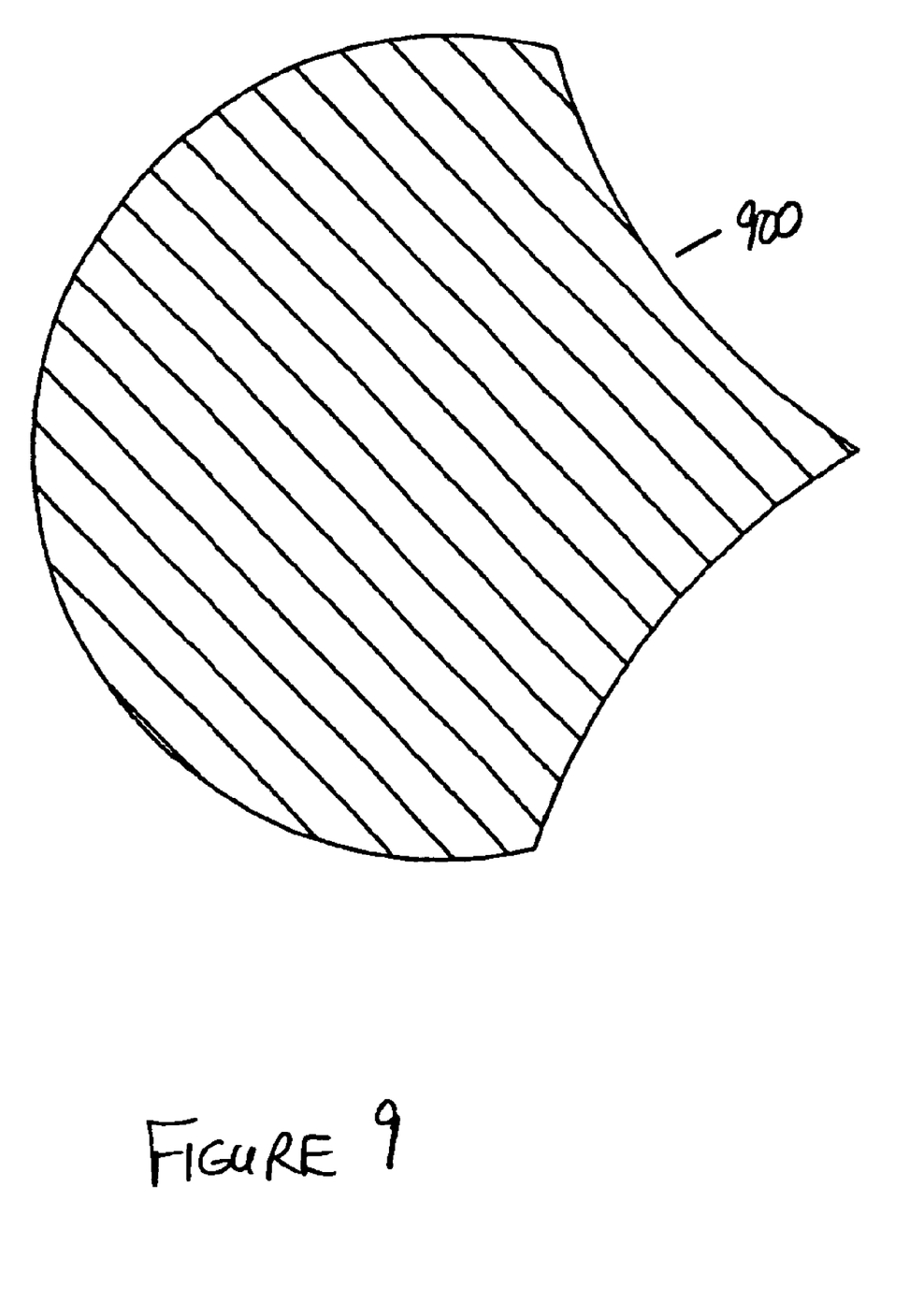
FIG. 9 is a cross-section of an energy conduit configured for at least one of cutting, separating, and parting tissue as it is pressed or forced against the tissue, under an embodiment.

FIG. 9 is a cross-section of an energy conduit 900 configured for at least one of cutting, separating, and parting tissue as it is pressed or forced against the tissue, under an embodiment. The energy conduit 900 is used to form the energy conduits 108 described above with reference to FIGS. 1. As the energy conduits 900 are advanced from the retracted state (FIG. 3) to the deployed or expanded state (FIG. 4), the energy conduits 900 penetrate or separate the surrounding tissue. This penetration is accomplished in one embodiment using energy conduits that have a geometry suited for separating or cutting the surrounding tissue. The penetration of tissue by the energy conduits 900 in an alternative embodiment is accomplished with the application of energy, for example RF energy, to the energy conduit 900 in order to facilitate cutting through the tissue during advancement of the energy conduits. Another alternative embodiment includes the use of both an energy conduit 900 having a cutting geometry along with the application of a suitable electrical energy to the energy conduit 900.

Figure 10:
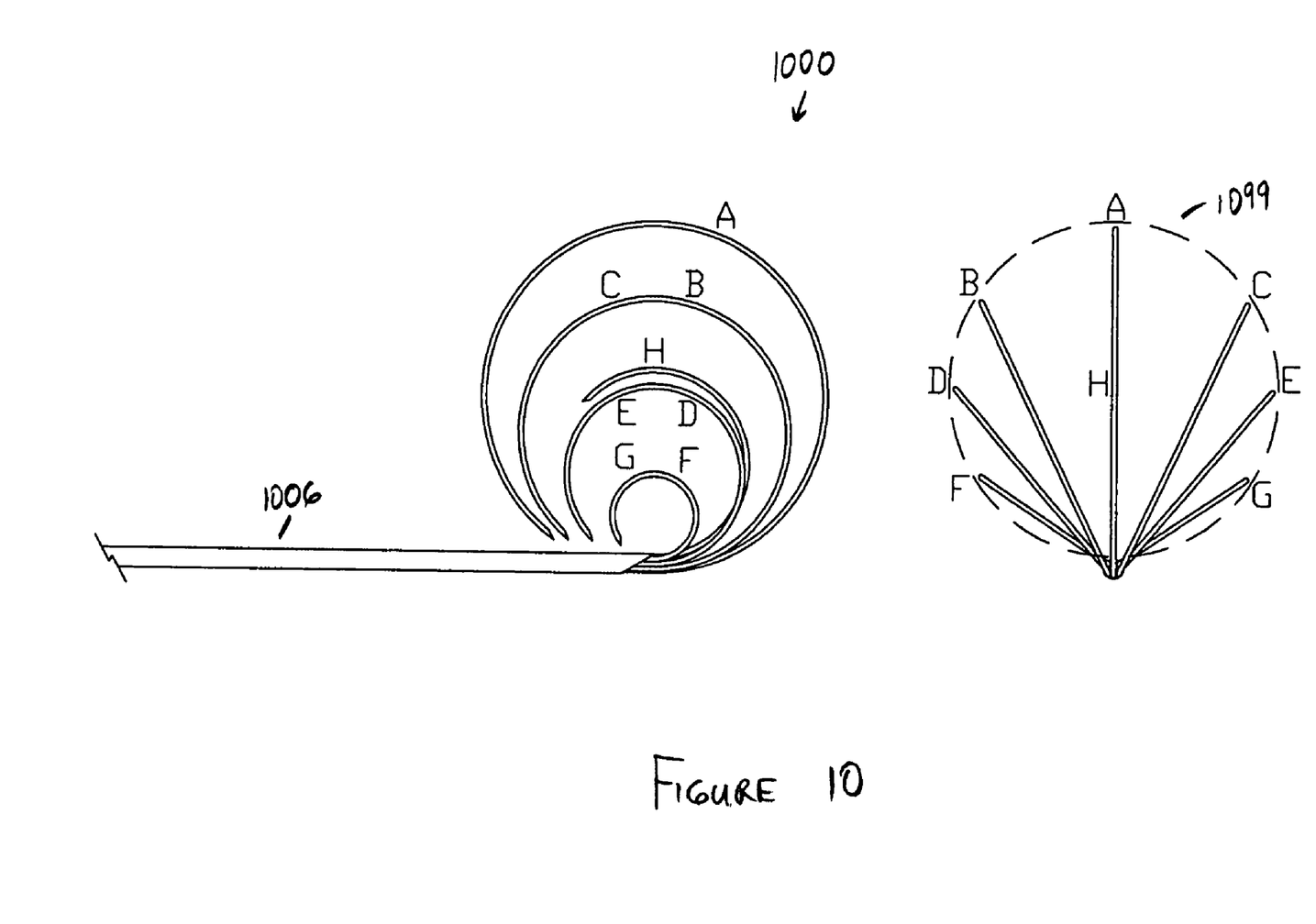
FIG. 10 is a distal portion of a tissue ablation device including a delivery member/tube and a plurality of energy conduits in a deployed state, under an alternative embodiment.

FIG. 10 is a distal portion 1000 of a tissue ablation device including a delivery member/tube and a plurality of energy conduits A, B, C, D, E, F, and G (collectively referred to as A-G) in a deployed state, under an alternative embodiment. The energy conduits A-G comprise nickel titanium alloy, for example, but can be formed from any number/combination of materials. Further, the outside diameter of the energy conduits A-G of an embodiment is approximately in the range of 0.010 to 0.040 inches, but is not so limited.

As described above, the delivery member/tube 1006 provides sufficient support for placement of the energy conduits A-G. Advancement of a deployment slider (not shown) advances and deploys the energy conduits A-G to a deployed shape. The shape of these energy conduits A-G can form a series of approximately semi-spherical segments which in this embodiment when taken together form the outline of a sphere 1099 that fully encompasses a volume of tissue targeted for ablation. The application of RF energy to the energy conduits A-G generates or produces a spherical volume of ablated tissue. The energy conduits A-G of an embodiment are configured to each have an alternating electrical polarity. The energy conduits of an alternative embodiment are of a single electrical polarity, with the delivery member/tube 1006 conducting an opposite polarity. In still another alternative embodiment, the energy conduits A-G are individually switched between the same electrical polarity and the delivery member/tube 1006 conducts an opposite/alternating polarity to that of the energy conduits A-G. In yet another alternative embodiment, the delivery member/tube 1006 and energy conduits A-G are of a single electrical polarity and one or more secondary grounding pads are used therewith to provide an opposite polarity member.

In operation, the tissue ablation system of an embodiment delivers energy to target tissue via the energy conduits A-G. The energy includes, for example, radio frequency (RF) energy, but is not so limited. The energy is delivered via any of a number of techniques. The energy can be applied via pulsed waveforms and/or continuous waveforms, but is not so limited.

In an example procedure that includes use of the tissue ablation system, energy can be applied to energy conduits A-G during deployment of the energy conduits A-G into the target tissue. The energy can be applied automatically or, alternatively, manually as a procedure progresses and as appropriate to the procedure. Also, the energy delivered to the target tissue can be adjusted during the procedure by adjusting any of the power level, the waveforms, and a combination of the power level and the waveform.

In another example procedure that includes use of the tissue ablation system, energy can be applied to energy conduits A-G following deployment of the energy conduits A-G into the target tissue. The energy can be applied automatically or, alternatively, manually as appropriate to the procedure. Also, the energy delivered to the target tissue can be adjusted manually and/or automatically during the procedure by adjusting any of the power level, the waveforms, and a combination of the power level and the waveform.

In addition to the components of the tissue ablation device 1000, various sensing techniques can be used to guide or control the progress of the tissue ablation. For example temperature sensors can be imbedded or attached to at least one of the energy conduits A-G and the delivery member/tube 1006 to provide feedback to a user and/or an energy controller. Additionally, a variety of sensors can be deployed from the tissue ablation device 1000 into tissue of the target tissue.

In addition to the components of the tissue ablation systems described above, various sensing techniques can be used with and/or coupled to the tissue ablation system to guide or control the progress of the tissue ablation. For example temperature sensors can be imbedded or attached to the deployable energy conduits and provide feedback to a user or an energy controller. A variety of sensors can also be deployed from the device into tissue within the targeted tissue, in this case a sphere.

Figure 11:
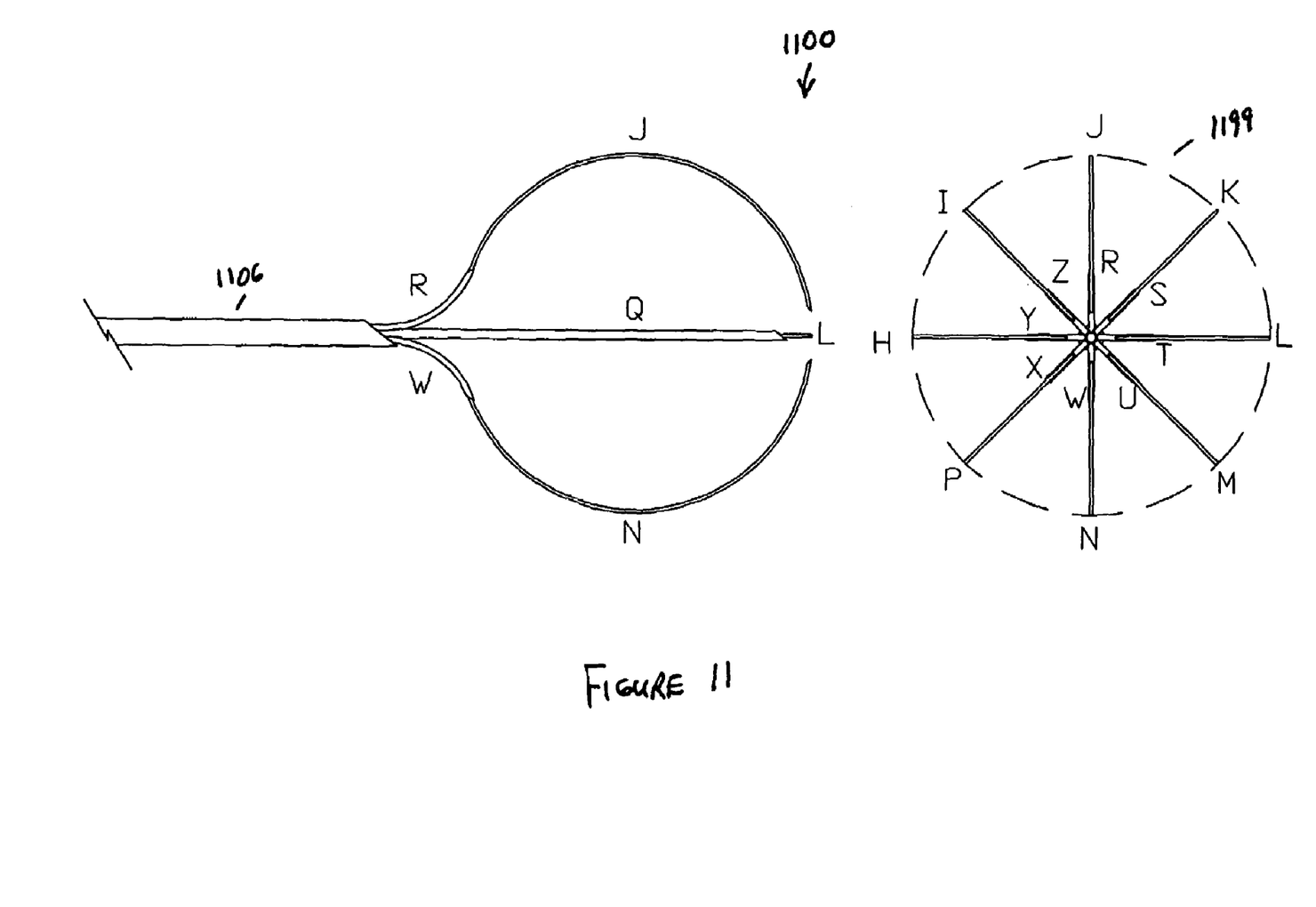
FIG. 11 is a distal portion of a tissue ablation device including a delivery member/tube and a plurality of energy conduits in a deployed state, under yet another alternative embodiment.

FIG. 11 is a distal portion 1100 of a tissue ablation device including a delivery member/tube 1106, a plurality of primary energy conduits R, S, T, U, W, X, Y, Z (collectively referred to as R-Z), and a plurality of secondary energy conduits H, I, J, K, L, M, N, and P (collectively referred to as H-P) and Q in a deployed state, under yet another alternative embodiment. For clarity electrodes H, I, K, M, P, S, T, U, X, Y, and Z have been omitted in the side view of the device shown in FIG. 11. The primary R-Z and secondary H-P energy conduits comprise nickel titanium alloy, for example, but can be formed from any number/combination of materials some of which are described above. Further, the outside diameter of the primary R-Z and secondary H-P energy conduits of an embodiment is approximately in the range of 0.010 to 0.080 inches, but is not so limited.

As described above, the delivery member/tube 1106 provides sufficient support for placement of the primary energy conduits R-Z. Likewise the primary energy conduits R-Z provide sufficient support for placement of the secondary energy conduits H-P. While the tissue ablation device of an embodiment deploys one secondary energy conduit from one or more distal and/or lateral ports in a distal region of each primary energy conduit, alternative embodiments of the tissue ablation device can deploy more than one secondary energy conduit from one or more distal and/or lateral ports of each primary energy conduit. Advancement of a deployment slider (not shown) as described above advances and deploys the energy conduits R-Z, H-P, and Q to a deployed state or shape in target tissue. The energy conduits R-Z, H-P in a deployed state form a series of approximately semi-spherical segments which when taken together in this embodiment form the outline of a sphere 1199 that fully encompasses a volume of tissue targeted for ablation. The application of RF energy to the energy conduits R-Z, H-P, and Q generates or produces a spherical volume of ablated tissue.

The energy conduits R-Z, H-P, and Q of an embodiment are configured to each have an alternating electrical polarity. The energy conduits of an alternative embodiment conduct electrical energy of a single electrical polarity, with the delivery member/tube 1106 conducting electrical energy having an opposite polarity. In still another alternative embodiment, the energy conduits H-P and R-Z are individually switched between the same electrical polarity and electrode Q is coupled to conduct electrical energy of an opposite/alternating polarity to that of the energy conduits H-P and R-Z. In yet another alternative embodiment, all energy conduits R-Z, H-P, and Q are of a single electrical polarity and one or more secondary grounding pads are used therewith to provide an opposite polarity member. In still another embodiment, electrode Q is not present and energy passes within the remaining electrodes.

In operation, the tissue ablation system of an embodiment delivers energy to target tissue via the energy conduits R-Z, H-P, and Q. The energy includes, for example, radio frequency (RF) energy, but is not so limited. The energy is delivered via any of a number of techniques, some of which are described herein. The energy can be applied via pulsed waveforms and/or continuous waveforms, but is not so limited.

In an example procedure that includes use of the tissue ablation system, energy can be applied to energy conduits R-Z, H-P, and Q during deployment of the energy conduits R-Z, H-P, and Q into the target tissue. The energy can be applied automatically or, alternatively, manually as a procedure progresses and as appropriate to the procedure. Also, the energy delivered to the target tissue can be adjusted during the procedure by adjusting any of the power level, the waveforms, and a combination of the power level and the waveform.

In another example procedure that includes use of the tissue ablation system, energy can be applied to energy conduits R-Z, H-P, and Q following deployment of the energy conduits R-Z, H-P, and Q into the target tissue. The energy can be applied automatically or, alternatively, manually as appropriate to the procedure. Also, the energy delivered to the target tissue can be adjusted manually and/or automatically during the procedure by adjusting any of the power level, the waveforms, and a combination of the power level and the waveform.

In addition to the components of the tissue ablation device 1100, various sensing techniques can be used to guide or control the progress of the tissue ablation. For example temperature sensors can be imbedded or attached to at least one of the energy conduits R-Z, H-P, and Q and the delivery member/tube 1106 to provide feedback to a user and/or an energy controller. Additionally, a variety of sensors can be deployed from the tissue ablation device 1100 into tissue of the target tissue.

In addition to the components of the tissue ablation systems described above, various sensing techniques can be used with and/or coupled to the tissue ablation system to guide or control the progress of the tissue ablation. For example temperature sensors can be imbedded or attached to the deployable energy conduits and provide feedback to a user or an energy controller. A variety of sensors can also be deployed from the device into tissue within the targeted tissue, in this case a sphere.

Figure 12:
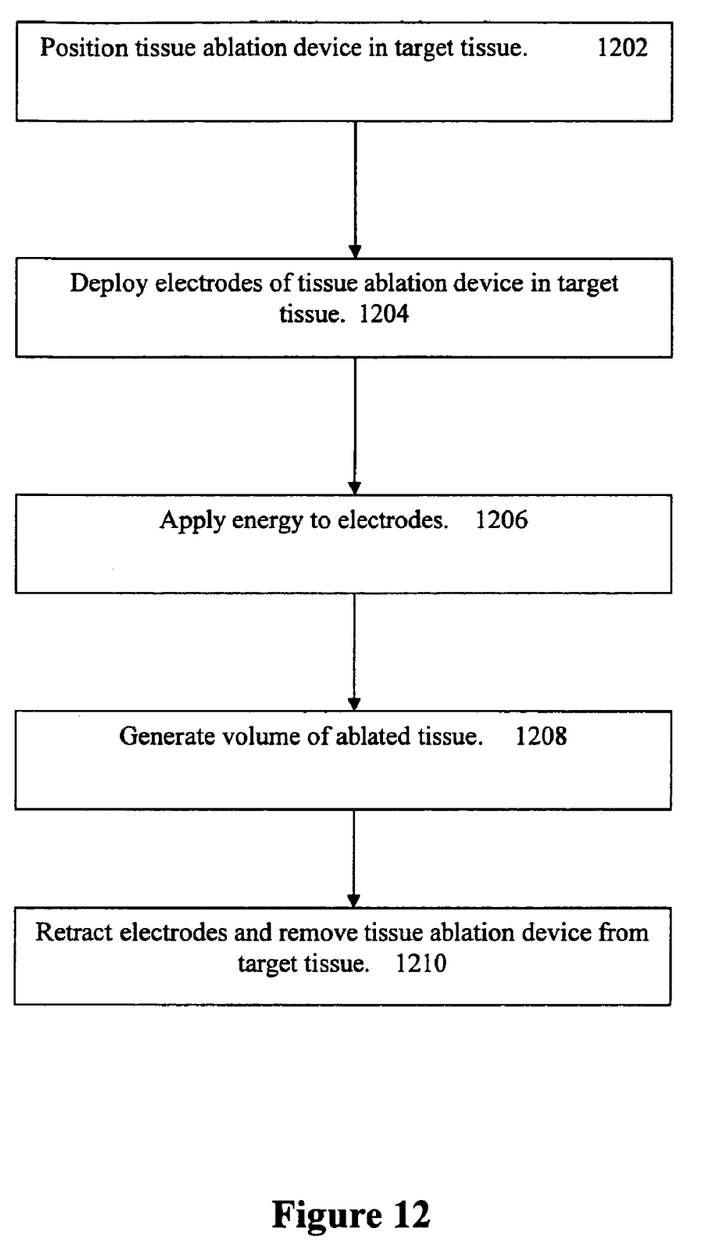
FIG. 12 is a flow diagram of tissue ablation procedure using the tissue ablation device, under an embodiment.

FIG. 12 is a flow diagram of tissue ablation procedure using the tissue ablation device, under an embodiment. In operation generally a user positions the tissue ablation device in the target biological tissue as appropriate to a medical procedure, at block 1202. Placement of the tissue ablation device in the target tissue can include the use of various visualization methods such as ultrasound stenography, Computerized Tomography (CT), and Magnetic Resonance Imaging (MRI), but is not so limited.

Following placement of the device in the target tissue the user deploys the electrodes in the target tissue, at block 1204. Power or energy is applied to the target tissue via the electrodes, at block 1206. The energy generates a volume of ablated tissue having a shape and size appropriate to the configuration of the deployed electrodes, at block 1208. The user retracts the electrodes and removes the device from the target tissue, at block 1210.

As described above, the tissue ablation system of an embodiment delivers energy to target tissue via the energy conduits or electrodes. The energy includes, for example, radio frequency (RF) energy, but is not so limited. The energy is delivered via any of a number of techniques. The energy can be applied via pulsed waveforms and/or continuous waveforms, but is not so limited.

In an example procedure that includes use of the tissue ablation system, energy can be applied to energy conduits during deployment of the energy conduits into the target tissue. The energy can be applied automatically or, alternatively, manually as a procedure progresses and as appropriate to the procedure. Also, the energy delivered to the target tissue can be adjusted during the procedure by adjusting any of the power level, the waveforms, and a combination of the power level and the waveform.

In another example procedure that includes use of the tissue ablation system, energy can be applied to energy conduits following deployment of the energy conduits into the target tissue. The energy can be applied automatically or, alternatively, manually as appropriate to the procedure. Also, the energy delivered to the target tissue can be adjusted manually and/or automatically during the procedure by adjusting any of the power level, the waveforms, and a combination of the power level and the waveform.

As described above, the application of power to the target tissue under an embodiment is controlled automatically and/or manually under a number of procedures. A first type of procedure uses a predetermined pattern of energy delivery according to a time schedule. A second type of procedure varies the application of energy to the target tissue volume in accordance with temperature information or feedback parameters of the tissue. A third type of procedure varies the application of energy to the target tissue volume in accordance with impedance information or feedback parameters of the tissue in combination with elapsed time. A fourth type of procedure varies the application of energy to the target tissue volume in accordance with impedance information or feedback parameters of the tissue. A fifth type of procedure varies the application of energy to the target tissue volume in accordance with temperature and impedance information or feedback parameters of the tissue.

Note that patent and procedure selection is the responsibility of the medical professional/user and the outcome is dependent on many variables, including patient anatomy, pathology, and surgical techniques. Use of the tissue ablation device, system and methods described herein for tissue ablation can result in localized elevated temperatures that can cause thermal injury to the skin. In addition, tissue or organs adjacent to the tissue being ablated may be injured thermally. To minimize the potential for thermal injury to the skin or adjacent tissues, temperature-modifying measures can be initiated at the physician's discretion. These may include applying a sterile ice pack or saline-moistened gauze to cool and/or separate tissues, but are not so limited.

Unless the context clearly requires otherwise, throughout the description and the claims, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. Additionally, the words "herein," "hereunder," "above," "below," and words of similar import refer to this application as a whole and not to any particular portions of this application. When the word "or" is used in reference to a list of two or more items, that word covers all of the following interpretations of the word: any of the items in the list, all of the items in the list and any combination of the items in the list.

The above description of illustrated embodiments of the tissue ablation devices and methods is not intended to be exhaustive or to limit the systems and methods to the precise form disclosed. While specific embodiments of, and examples for, the tissue ablation devices and methods are described herein for illustrative purposes, various equivalent modifications are possible within the scope of the systems and methods, as those skilled in the relevant art will recognize. The teachings of the tissue ablation devices and methods provided herein can be applied to other medical systems, not only for the medical systems described above.

The elements and acts of the various embodiments described above can be combined to provide further embodiments. These and other changes can be made to the tissue ablation devices and methods in light of the above detailed description.

The above references and United States Patent applications are incorporated herein by reference. Aspects of the tissue ablation devices and methods can be modified, if necessary, to employ the systems, functions and concepts of the various patents and applications described above to provide yet further embodiments of the tissue ablation devices and methods.

In general, in the following claims, the terms used should not be construed to limit the tissue ablation devices and methods to the specific embodiments disclosed in the specification and the claims, but should be construed to include all medical devices and systems that operate under the claims to provide tissue ablation and/or tissue resection. Accordingly, the tissue ablation devices and methods are not limited by the disclosure, but instead the scope of the systems and methods is to be determined entirely by the claims.

While certain aspects of the tissue ablation devices and methods are presented below in certain claim forms, the inventors contemplate the various aspects of the systems and methods in any number of claim forms. Accordingly, the inventors reserve the right to add additional claims after filing the application to pursue such additional claim forms for other aspects of the tissue ablation devices and methods.

What is claimed is:

1. An ablation device, comprising:
an electrode array including,
a conductive central deployment member; and
a plurality of electrodes arranged in an alternating polarity series so that adjacent electrodes have opposite polarities, wherein distal ends of each of the electrodes are connected to each of a plurality of distal insulators, wherein each distal insulator is connected to a retaining disk that is non-conductive, wherein the retaining disk is connected to a distal end of the conductive central deployment member; and
a delivery member slidably coupled about the conductive central deployment member, wherein the delivery member is rigid, wherein proximal ends of each of the electrodes are fixed to a distal end of the delivery member such that sliding the delivery member deploys the plurality of electrodes from a retracted state to a deployed state in which the electrodes form a relatively spherical shape in a tissue volume.

2. The device of claim 1, wherein the electrodes are further configured for coupling to an energy source.

3. The device of claim 1, wherein the plurality of electrodes are bipolar electrodes.

4. The device of claim 1, wherein one or more of the electrodes include at least one internal lumen.

5. The device of claim 1, further comprising at least one sensor.

6. The device of claim 1, wherein the retaining disk comprises a circular disk having a plurality of electrode apertures positioned around an outer region of the retaining disk, each electrode aperture sized to receive a distal insulator connected to an electrode, wherein the retaining disk includes a center aperture that receives the distal end of the conductive central deployment member, wherein a distal tip secures the retaining disk to the conductive central deployment member.

7. The device of claim 1, comprising a plurality of proximal insulators, wherein each proximal insulator is connected to the proximal end of one electrode.

8. The device of claim 1, wherein the conductive central deployment member is an electrode having a same polarity as a set of the plurality of electrodes.

9. The device of claim 1, wherein a diameter of the spherical shape of the plurality of electrodes in the deployed state is approximately in a range of 3.1 centimeters to 9 centimeters.

10. A tissue ablation device, comprising:
a handle;
a delivery member coupled to the handle, wherein the delivery member is rigid;
an energy delivery device including,
a deployment member coupled to the handle and slidably coupled to the delivery member such that the delivery member slides distally and proximally with respect to the deployment member, wherein the deployment member is rigid and conductive,
a plurality of electrodes that are arranged about the deployment member in an alternating polarity series so that adjacent electrodes have opposite polarities, and configured for coupling to an energy source, wherein a distal end of each of the electrodes is connected to a distal insulator, wherein the distal insulator is connected to a retaining disk that is non-conductive, wherein the retaining disk is connected to the distal end of the deployment member, and a proximal end of each of the electrodes is fixed to distal end of the delivery member, wherein the plurality of electrodes are dynamically configurable between a retracted state and a deployed state by sliding the delivery member, wherein the retracted state positions the electrodes in a relatively straight configuration approximately parallel to the deployment member, wherein the deployed state configures the electrodes in a relatively spherical configuration.

11. The device of claim 10, wherein the energy source includes a radio frequency (RF) generator.

12. The device of claim 10, comprising a plurality of proximal insulators, wherein each proximal insulator is connected to the proximal end of one electrode.

13. An ablation system, comprising:
an energy source; and
a tissue ablation device comprising an electrode array coupled to a distal end of an introducer, wherein the introducer is rigid, the electrode array including a support member having a distal end configured to penetrate tissue and a plurality of electrodes coupled to the energy source, wherein the plurality of electrodes is arranged in an alternating polarity series so that adjacent electrodes have opposite polarities, wherein the support member is conductive, wherein proximal ends of each electrode are fixed to a slidable member that slides over the support member, and distal ends of each electrode are connected to each of a plurality of distal insulators, wherein each distal insulator is connected to a retaining disk that is non-conductive, wherein the retaining disk is connected to and electrically isolated from a distal end of the support member, wherein the plurality of electrodes are dynamically configurable from a retracted state by sliding the slidable member distally to a deployed state in which the electrodes form a relatively spherical shape in a tissue volume.

14. The system of claim 13, wherein the energy source comprises a radio frequency (RF) generator, and wherein the plurality of electrodes comprises bipolar electrodes, the system further comprising a controller coupled among the RF generator and the bipolar electrodes to provide automatic control of energy delivery to each of the bipolar electrodes.

15. The system of claim 13, wherein the retracted state positions the electrodes in a relatively straight configuration approximately parallel to the support member.

16. The system of claim 13, wherein the electrodes couple energy from the energy source to the tissue volume, wherein the energy is controlled in response to at least one of elapsed time of energy delivery, a temperature of the target tissue, and an impedance of the target tissue, wherein the energy coupled to the target tissue ablates a spherical volume of the target tissue.

17. The system of claim 13, comprising a plurality of proximal insulators, wherein each proximal insulator is connected to the proximal end of one electrode.

18. The system of claim 13, wherein power output of the energy source is less than 2,500 Watts.

19. The system of claim 13, wherein an outside diameter of each electrode of the plurality of electrodes is approximately in a range of 0.005 inches to 0.093 inches.

* * * * *